(12) United States Patent
Scheibner et al.

(10) Patent No.: US 10,036,052 B2
(45) Date of Patent: Jul. 31, 2018

(54) METHOD FOR PRODUCING BIOGENIC SUBSTANCES

(71) Applicant: BRANDENBURGISCHE TECHNISCHE UNIVERSITÄT COTTBUS-SENFTENBERG, Senftenberg (DE)

(72) Inventors: Katrin Scheibner, Senftenberg (DE); Jan-Heiner Küpper, Großkoschen (DE); Kai-Uwe Schmidtke, Jena (DE); Sebastian Miethbauer, Jena (DE); Natalie Herzog, Cottbus (DE)

(73) Assignee: Brandenburgische Technische Universität Cottbus-Senftenberg, Senftenberg (DE)

( * ) Notice: Subject to any disclaimer, the term of this patent is extended or adjusted under 35 U.S.C. 154(b) by 0 days.

(21) Appl. No.: 15/035,927

(22) PCT Filed: Nov. 11, 2014

(86) PCT No.: PCT/EP2014/074278
§ 371 (c)(1),
(2) Date: May 11, 2016

(87) PCT Pub. No.: WO2015/071264
PCT Pub. Date: May 21, 2015

(65) Prior Publication Data
US 2016/0289724 A1     Oct. 6, 2016

(30) Foreign Application Priority Data

Nov. 12, 2013  (EP) .................................... 13192606

(51) Int. Cl.
*C12P 19/60* (2006.01)
*C12P 13/00* (2006.01)

(52) U.S. Cl.
CPC .......... *C12P 19/605* (2013.01); *C12P 13/001* (2013.01); *C12P 13/005* (2013.01); *C12P 19/60* (2013.01); *C12Y 106/02004* (2013.01)

(58) Field of Classification Search
None
See application file for complete search history.

(56) References Cited

U.S. PATENT DOCUMENTS

| | | | |
|---|---|---|---|
| 6,555,107 B2 | 4/2003 | Poeschla et al. | |
| 2010/0260731 A1 | 10/2010 | Braspenning et al. | |
| 2013/0323721 A1 | 12/2013 | Braspenning et al. | |

FOREIGN PATENT DOCUMENTS

| | | |
|---|---|---|
| CN | 103374573 A | 10/2013 |
| DE | 698 30 663 T2 | 5/2006 |
| DE | 10 2007 058 741 A1 | 6/2009 |
| DE | 10 2008 034 829 A1 | 2/2010 |
| EP | 1 175 436 A2 | 1/2002 |
| WO | WO-00/61617 A2 | 10/2000 |
| WO | WO-02/40995 A2 | 5/2002 |
| WO | WO-2008/119780 A2 | 10/2008 |
| WO | WO-2009/007678 A2 | 1/2009 |
| WO | WO-2009/030217 A2 | 3/2009 |
| WO | WO-2010/123357 A1 | 10/2010 |
| WO | WO-2012/045731 A1 | 4/2012 |

OTHER PUBLICATIONS

Kinne et al., "Regioselective preparation of 5-hydroxypropanolol and 4'-hydroxydiclofenac with a fungal peroxygenase", Bioorganic & Medicinal Chemistry Letters 2009, vol. 19, pp. 3085-3087.*
Mueller et al., "Biotransformation of diclofenac and effects on the metabolome of primary human hepatocytes upon repeated dose exposure", European Journal of Pharmaceutical Sciences 2012, vol. 45, pp. 716-724.*
Darnell et al., "In Vitro Evaluation of Major In Vivo Drug Metabolic Pathways Using Primary Human Hepatocytes and HepaRG Cells in Suspension and a Dynamic Three-Dimensional Bioreactor System", Journal of Pharmacology and Experimental Therapeutics 2012, vol. 343, pp. 134-144.*
International Search Report for PCT/EP2014/074278 dated Mar. 5, 2015.
Sells, M. A., et al., "Production of Hepatitis B Virus Particles in Hep G2 Cells Transfected with Cloned Hepatitis B Virus DNA", Proc. Natl. Acad. Sci. USA, 1987, vol. 84, pp. 1005-1009.
International Preliminary Report on Patentability for PCT/EP2014/074278 dated May 17, 2016.
Alam, T., et al., "Glucose-Regulated Insulin Production in Hepatocytes", Transplantation, 2002, vol. 74, No. 12, pp. 1781-1787.

* cited by examiner

*Primary Examiner* — Michelle F. Paguio Frising
(74) *Attorney, Agent, or Firm* — Drinker Biddle & Reath LLP

(57) ABSTRACT

This invention relates to a biogenic substance production process wherein a) at least one starting material has b) at least one enzyme added to it and the product resulting from b) has c) at least one liver cell added to it, and d) at least one biogenic substance is isolated.

12 Claims, 6 Drawing Sheets

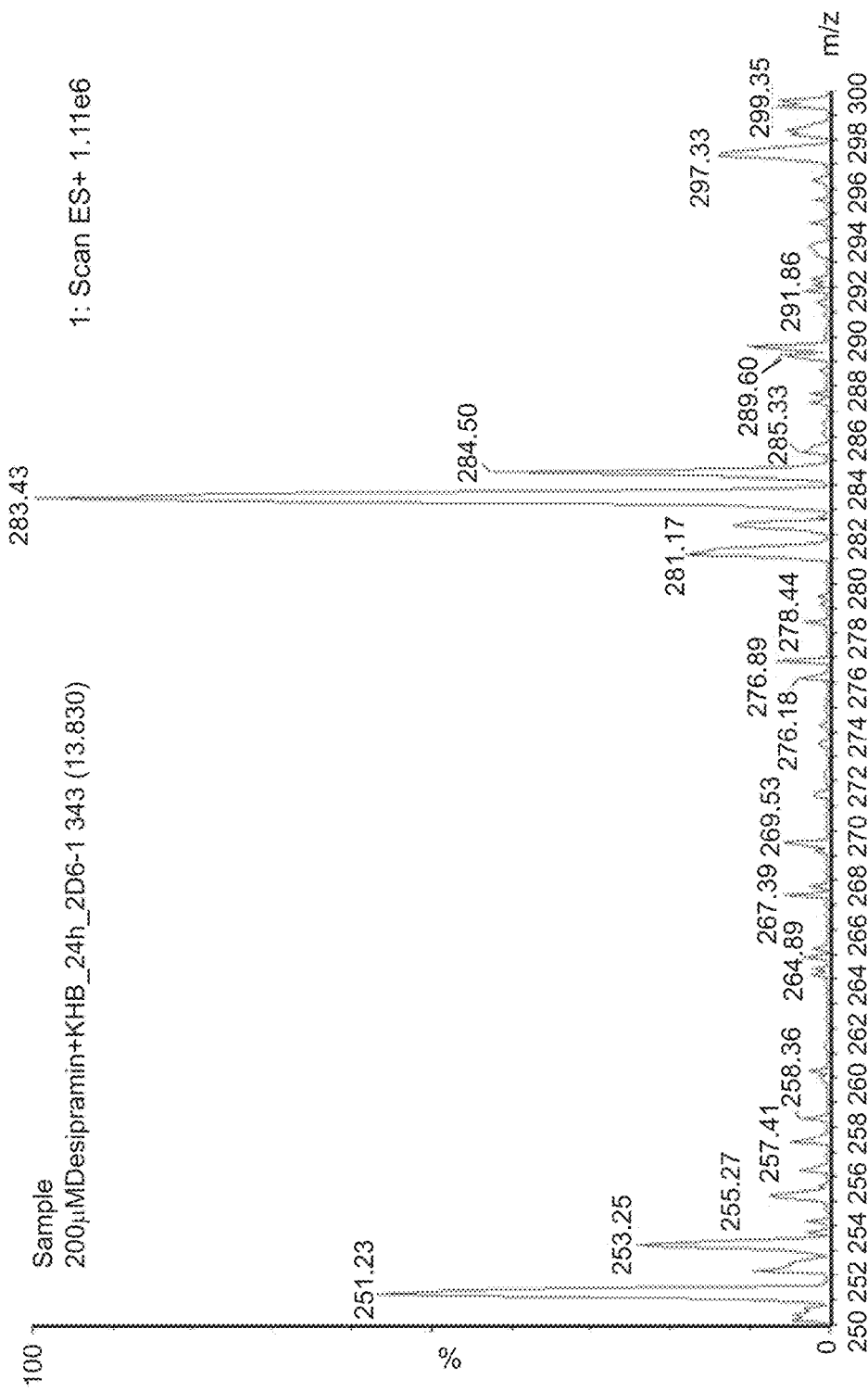

Figure 1:
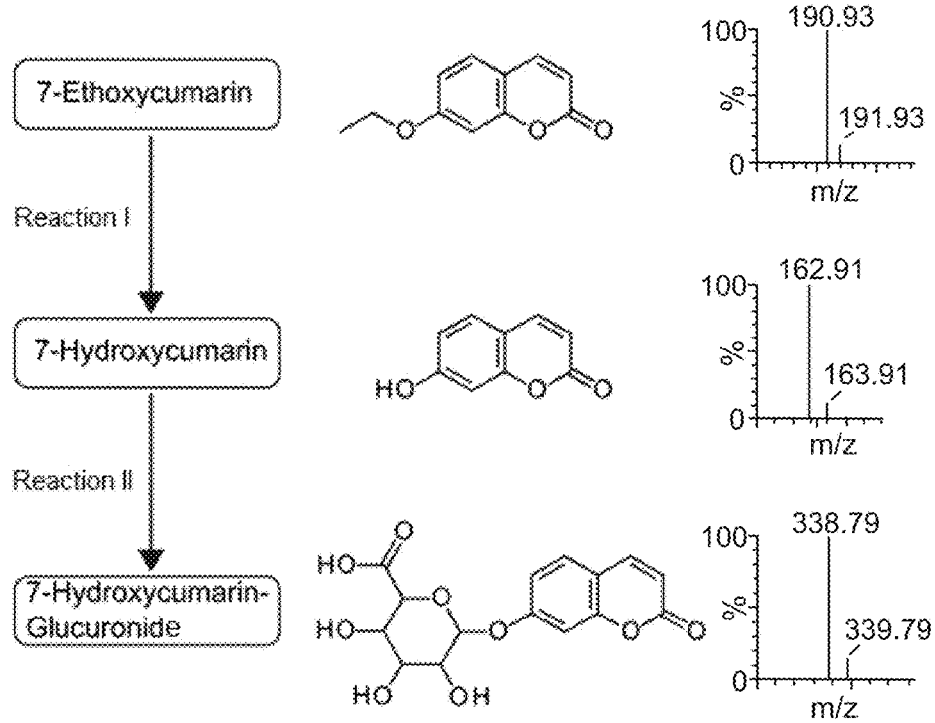

Propanolol → 5-OH-propanolol (Phase I metabolite) → 5-OH-propanolol 6-β-glucuronide (Phase II metabolite)

METHOD FOR PRODUCING BIOGENIC SUBSTANCES

The object of the invention is a process to produce biogenic substances.

There is great need for improved manufacturing processes for biogenic substances. It is especially preferred to produce biogenic substances that arise during the biotransformation or metabolism in liver cells (hepatocytes) or in the liver.

The liver is a central detoxification organ of the metabolism. Liver cells (hepatocytes) represent 70-80% of all cells in the liver and perform important physiological liver functions (Elaut et al. (2006)).

The liver uses biotransformation or metabolism to be able to eliminate or detoxify absorbed substances (e.g., medications, toxins, natural substances). For biotransformation, the phase I enzymes of the cytochrome P-450 (CYP450) system are especially important. The CYP450 enzymes are oxidoreductases, which cause oxidative breakdown or metabolism of numerous substances, such as medicinal substances, among others. Among the numerous CYP450 isoenzymes with different substrate specificity that humans have, the isoenzymes CYP1A2, -2C9, -2C19, -2D6, -2E1, and -3A4 alone are responsible for around 90% of all oxidative metabolism of medications (Arimoto (2006); Shimada et al. (1994); Lamb et al. (2007)). In many cases, many medications only acquire their curative efficacy, or even cause toxic metabolites with undesired drug reactions, once they have undergone these biochemical changes (Chang et al. 2007).

These substances are most interesting as breakdown products of the liver, and require further investigation. This requires producing such liver metabolites in sufficient quantity, in particular these biogenic substances have a high regiospecificity and stereospecificity. Such stereoisomers have regioselective and also stereoselective modifications, which are characteristic of biotransformation enzymes, as described below.

For biotransformation or metabolism in liver cells, phase I enzymes are described, in particular those of the cytochrome P-450 (CYP450) system, so-called oxidoreductases. Phase II enzymes, such as, e.g., N-acetyltransferases [NATs], UDP-glucuronosyltransferases, and sulfotransferases are also relevant. The activity of the phase I enzymes and phase II enzymes and other liver functions are of decisive importance for evaluation of the hepatotoxicity of substances.

Furthermore, it is significant that such biotransformation enzymes can also occur in other organisms, such as fungi and bacteria, as a result of evolution.

WO 2008/119780 A2 describes a process for enzymatic hydroxylation of non-activated hydrocarbons, in particular aromatic rings of non-activated hydrocarbon molecules (for example, the selective conversion of naphthalene to 1-naphthol) using fungal peroxidases from Basidiomycetes of the family Bolbitiaceae (e.g., *Agrocybe* spp.) to produce pharmaceuticals, terpenes, steroids, or fatty acids.

DE102008034829 A1 discloses a one-step enzymatic process for regioselective hydroxylation of 2-phenoxypropionic acid to 2-(4-hydroxyphenoxy)propionic acid. The enantioselective and regioselective monohydroxylation of 2-phenoxypropionic acid to 2-(4-hydroxyphenoxy)propionic acid by isolated biocatalysts (in vitro) can also [be carried out] by *Agrocybe aegerita* peroxygenase (AaP), a stable extracellular fungal enzyme, [which can] convert 2-phenoxypropionic acid in a highly regioselective manner to 2-(4-hydroxyphenoxy)propionic acid, and preferably to its (R)-enantiomer.

The prior art does not describe the production of biogenic substances by means of the coupling of enzymes and liver cells.

A disadvantage of the prior art is that biogenic substances cannot be produced in sufficient yield and variety. In addition, the prior art mostly involves the synthesis of precursor molecules. In addition, semisynthetic processes are often required, so that it can take a great deal of effort to introduce into the substance(s) the required further regioselective and stereoselective modifications which are decisive for metabolites from the liver.

Therefore, the invention relates to the production of biogenic substances that can be produced according to a novel process.

An essential aspect of the invention is that the synthesis of biogenic substances is carried out using enzymes in combination with a liver cell system.

Therefore, the object of the invention is a process to produce biogenic substances, characterized in that a) at least one starting material has b) at least one enzyme added to it and the product resulting from b) has c) at least one liver cell added to it, or b') at least one liver cell added to it and the product resulting from b) has c') at least one enzyme added to it, and d) at least one biogenic substance is isolated. (referred to elsewhere in this document as the "inventive process")

Surprisingly, liver-relevant biogenic substances can be economically produced in a continuous or discontinuous manner and in high yield, and it is advantageously possible to produce new stereoselective compounds (metabolites).

The starting materials or reactant(s) contain at least one chemical substance, a mixture of substances, in particular a pharmaceutical or active ingredient. The chemical substances are preferably organic molecules, which can contain, in addition to carbon (C) and hydrogen (H), heteroatoms, such as oxygen (O), nitrogen (N), sulfur (S), or phosphorus (P). The chemical substances can have linear and/or cyclic carbon chains, along with heteroatoms. It is preferable for the organic molecules to have [a density] less than 1,000 g/mol, especially less than 750 g/mol, less than 500 g/mol, or less than 250 g/mol. It is also preferable for at least one chemical substance to contain at least one chiral carbon atom.

The term "biogenic substances" as used in this invention means that the inventive process allows the production of substances or chemical substances, preferably von novel stereoisomers.

The chemical substances are preferably organic molecules, which can contain, in addition to carbon (C) and hydrogen (H), heteroatoms such as oxygen (O), nitrogen (N), sulfur (S), and phosphorus (P). The chemical substance can have linear and/or cyclic carbon chains, along with heteroatoms. It is preferable for the organic molecules to have [a density] less than 1,000 g/mol, especially less than 750 g/mol, less than 500 g/mol, or less than 250 g/mol.

The starting materials as well as biogenic substances can be sufficiently analyzed, e.g., by means of combined analytical processes such as GC/LC-MS, IR, and NMR, and possibly undergo a structural elucidation. Especially mass spectroscopy allows a sufficient rapid identification of the aforementioned substances, such as, e.g., molar mass, etc.

An "enzyme" as defined in this invention is a protein that can catalyze one or more biochemical reactions. An inventive enzyme is able to produce a first (enzyme) product or products from starting materials (reactants)—a substrate. Liver-specific enzymes are contained in a liver cell.

In a preferred embodiment, the enzymes are selected from the group of oxidoreductases (EC 1.x.x.x), in particular monooxygenases, dioxygenases, oxidases, dehydrogenases, reductases, and peroxygenases. The peroxygenases are especially preferred. Furthermore, biotransformation enzymes are suitable, in particular phase I enzymes and/or phase II enzymes. Moreover, esterases (EC 3.1.x.x), hydrolases (EC 3.x.x.x), and transferases (EC 2.x.x.x) are suitable. Corresponding enzymes can be assigned using the known EC enzyme classes or nomenclature.

Furthermore, it is preferred that the enzyme from b) and c') come from a different organism than the liver cell does.

In a preferred embodiment, a first enzyme is obtained from fungi, yeasts, algae, or bacteria, and the liver cells used are preferably human hepatocytes. However, fungi are preferred in the inventive process.

The enzymes can be isolated and purified from the organisms according to known processes. Furthermore, such enzymes can be produced in a host using recombinant techniques.

The term "liver cell" as used in this invention means that the cell at least has enzymes for biotransformation, in particular phase I enzymes and/or phase II enzymes, and consequently sufficiently carries out a liver function. The liver cell is preferably one that can be obtained from human liver cells or mammalian liver cells. Such hepatocytes can be prepared, e.g., from the teaching of WO2009/030217A2 and WO2012/045731A1, comprising genetically modified hepatocytes that have, e.g., a proliferation gene, so-called proliferating liver cells.

The inventive process also comprises genetically modified liver cells that can be (transgenically) modified in any way. For example, such liver cells can be produced by means of viral vectors (e.g., Lentivirinae, e.g., DE 69830663 T2, EP 1175436 B1). The production of such genetically modified liver cells is known to the person skilled in the art, and preferably phase I and phase II enzymes can also be made available by recombinant techniques. Furthermore, the inventive process can comprise, but is not limited to, liver cell lines known to the person skilled in the art that are commercially available (www.cell-lines-service.de) Chang liver (a human liver cell line), Hep-G2 (a human hepatoma cell line), HuH-7 (a human hepatoblastoma cell line), PLC-PRF-5 (a human hepatoma cell line), SK-HEP-1 (a human liver adenocarcinoma cell line), as well as, e.g., Fa2N-4, Hep3B, BC2, and HepaRG. According to the inventive process the liver cells can also occur in the cell aggregate.

The phase I enzymes that are relevant to the inventive process include especially the cytochrome P450 system, alcohol dehydrogenases, aldehyde dehydrogenases, peroxidases, glutathione peroxidase, esterases, and hydrolases.

The phase II enzymes that are relevant to the inventive process include especially the glucuronyl transferases, sulfotransferases, glutathione S-transferase, methyltransferases, aminotransferases/transaminases, and acetyltransferases.

Process steps b) (b') and c) (c') can be carried out in a one-pot system. Such a one-pot system is preferably in the form of a bioreactor.

In another preferred embodiment, process steps b) (b') and c) (c') are spatially separated from one another, e.g., by means of two or more bioreactors that are separated from one another. This can also be done by one bioreactor that has two or more layers, at least one of the above-mentioned inventive process steps being carried out in each layer.

However, it is preferable for two or more independent bioreactors to be used, which preferably can be coupled together.

Therefore, the invention relates to an inventive process wherein at least one bioreactor, preferably two or more bioreactors, are used to carry out process steps b) (b') and c) (c'), and at least one step b) (b') and c) (c') can also be repeated or downstream.

The bioreactors can be equipped with an agitator and other usual contrivances. Bioreactors that are suitable for cultivation are those such as hollow fiber bioreactors, stirred tank reactors (fermenters), fluidized-bed reactors (aggregates or porous support materials), fixed-bed reactors with hollow fiber or flat membrane beds (the process is tangential flow filtration), plug-flow reactors, spinner bottle cultivation (see Horst Chmiel (ed.) Bioprozesstechnik [Bioprocess engineering], Heidelberg: Spektrum Akademischer Verlag, 2011). The bioreactors can contain a medium, culture medium or culture fluid, in particular such media that are suitable for liver cells. Suitable cell cultures and culture media that are relevant are known to the person skilled in the art, and are commercially available (see examples).

In another preferred embodiment, the bioreactors are coupled together. The coupling can be done, for example, by any connection of two or more bioreactors, e.g., along a flow gradient, wherein medium, culture fluid, or supernatant move from one bioreactor to another bioreactor.

To implement the invention, the enzymes described in b) and c') can be used in such a way that the enzymes are present in an enzyme membrane reactor or immobilized on any support. Furthermore, scaffolds, microsomes, or cell-free systems are suitable. The enzymes can also be fixed by means of collagen or gelatin.

The resulting biogenic substances (down-stream process) or intermediates can be isolated by disruption of the liver cells or purification from the supernatant (step d.)). The resulting products and compounds can be identified, e.g., by means of LC/MS.

The following examples and figures serve to explain the invention in detail, without, however, limiting the invention to these examples and figures.

EXAMPLES AND FIGURES

Example 1

Production of 4'-hydroxydiclofenac by Liver Cells

HepG2 cells (ATCC HB-8065) are cultivated in the medium DMEM PAA (Pasching, Austria), to which is added 10% FCS Gold, 2 mM L-glutamine, 100 U/mL penicillin, and 0.1 mg/mL streptomycin. Primary human hepatocytes (pHHs) are commercially obtained from, e.g., TebuBio (Le Perray-en-Yvelines, France) or Promocell (Heidelberg, Germany). The cells are seeded onto 50 µg/mL collagen type I (rat tail, BD Biosciences, San Jose, USA) coated cell culture plates and cultivated at 37° C. under 5% $CO_2$ in hepatocyte growth medium (Promocell GmbH, Heidelberg, Germany) or equivalent cell culture media of other manufacturers known to the person skilled in the art. These pHHs can be used for metabolite production immediately or after production of proliferation-competent liver cells. To accomplish this, proliferation genes are transduced into the cells using a lentiviral vector. This technique is described in WO2009/030217A2 (Braspenning et al. (2007)). Cell clones, which have, in contrast to uninfected primary hepatocytes, received proliferation capability, grow into colonies that are visible in the cell culture dishes, and can be detached and isolated through trypsinization. The proliferating hepatocyte clones (cell lines) are characterized with respect to their liver cell markers. Through quantitative real-time PCR (qRT-PCR) it is possible to detect that the enzymes necessary for the formation of phase I and phase II metabolites are expressed. For definition of sequences to generate primers, the person skilled in the art can use databases such as the NCBI GenBank® (http://www.ncbi.nlm.nih.gov/genbank) or the European Nucleotide Archive (http://www.ebi.ac.uk/ena/). For phase I, the most relevant enzymes are those of the cytochrome P450 (CYP) family. These include the CYPs 1A2, 2B6, 2C6, 2C8, 2C9, 2C19, 3A4, 3A5, 3A6, 2D5, and 2E1, among others. For phase II, the relevant enzymes are the UDP-glucuronosyltransferases (UGTs), sulfotransferases (STs), N-acetyltransferases (NATs), glutathione S-transferases (GSTs), and methyltransferases (e.g., TPMT, COMT etc.), among others. For all these phase I and phase II enzymes, suitable primers for detection through qRT-PCR can be derived from database entries (NCBI, ENA). Alternatively, the expression of the relevant enzymes of biotransformation can be detected through immunofluorescence or western blot using specific primary antibodies that bind to the expressed phase I and phase II enzymes.

A suitable hepatocyte culture, whether proliferation-competent hepatocytes (e.g., cell clone HepaFH3) or non-proliferation-competent pHHs are then seeded into collagen I-coated 24-well plates, e.g., $5 \times 10^5$ cells per well. After 2-7 days in culture, medium with 100 µM diclofenac (Sigma-Aldrich, St. Louis, USA) is added to the cells. The cells are incubated in hepatocyte medium for 2-24 hours in the incubator at 5% $CO_2$ and 37° C. Supernatants of these cell cultures are used for trace analysis with HPLC. To accomplish this, the instrument VWR-Hitachi Elite LaChrom series HPLC with photodiode array L-2455 (column: Phenomenex Kinetex C18, 4.6×150 mm, 5 µm particle size, 100 Å; precolumn: RP18; 4.6×2 mm) can be used. The resulting metabolite—4'-hydroxy-diclofenac—can also be detected through LC-MS using a Waters Alliance HPLC System (column: Phenomenex Luna C18[2] 2.0×150 mm, 5 µm particle size, 100 Å; precolumn: RP18; 4×3 mm) in combination with a ZMD SingleQuad-MS detection system (ESI+; cone voltage: 30 eV).

As is shown in Table 1, characteristic quantities of metabolites are found for each of HepaFH3 (proliferation-competent liver cells), HepG2 (liver cell line), and primary human hepatocytes (pHH) of various donors when they are used for the cell system.

TABLE 1

Metabolism of diclofenac and testosterone in various liver cell systems

| Substance | Metabolites | HepaFH3 (n = 6) | HepG2 (n = 3) | pHH donor 1 | pHH donor 2 |
|---|---|---|---|---|---|
| Diclofenac | 4'-OH-diclofenac | 7.13 ± 2.22 | n.d. | 15.3 | 59.4 |
| Testosterone | Androstenedione | 84.33 ± 11.59 | 35.32 ± 0.1 | 30.9 | 72.2 |
|  | OH-testosterone | 3.02 ± 1.06 | 2.76 ± 0.1 | 6.1 | 23.0 |

The values obtained through HPLC and LC-MS analysis are expressed in pmol/(min*$10^6$ cells);
n.d. = no metabolites detectable;
pHH = primary human hepatocytes Example 2

Production of the phase II metabolite 7-hydroxycumarin-glucuronide from 7-ethoxycumarin through a two-step process.

Figure 2:
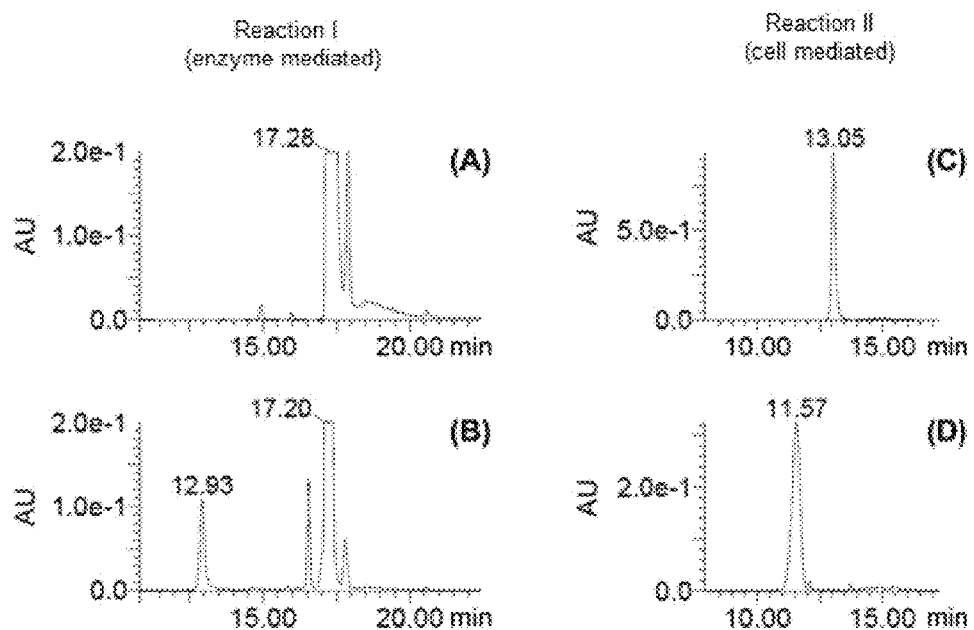

In this sample embodiment, the starting material 7-ethoxycoumarin was converted, in a first reaction, to the phase I metabolite 7-hydroxycoumarin, catalyzed by fungal peroxygenases. In a following reaction, this intermediate was biotransformed into the phase II metabolite (glucuronide) in a cell bioreactor. This second reaction is carried out on primary or molecular biologically modified human liver cells. This example illustrates the combined synthesis for human first-pass drug metabolites (phase I and II) from an enzyme- and cell-mediated biotransformation ((Ullrich et al. (2007); Kinne et al. (2009); Poraj-Kobielska et al. (2011)). FIG. 2 shows the principle of the reaction sequence. Reaction I was carried out using a reaction batch of 0.5-200 mL (0.5-5 mM substrate; peroxygenase of the fungus *Agrocybe aegerita* with an activity of 4-400 units; phosphate buffer 50 mM (pH 7); 4 mM ascorbic acid). After addition of the cosubstrate $H_2O_2$ (reaction activator; 5 mM) and a reaction time of 60 min., the resulting product (7-hydroxycoumarin) was determined by LC-MS ($\lambda$max=323 nm). Thus, this example involves an O-deethylation reaction of 7-ethoxycoumarin to the phase I metabolite 7-hydroxycoumarin. In the second reaction, cells (human hepatocytes) are used for biotransformation of 7-hydroxycoumarin to the phase II metabolite 7-hydroxycoumarin glucuronide (Braspenning et al. (2007); Hansen et al. (2013); Burkard et al. (2012)). The hepatocytes were preincubated for at least 7 days in a hollow fiber bioreactor (CellFiber-System; area: 75 $cm^2$; cell count: $1 \times 10^8$ cells). Then, the substrate (100 µM) was applied through a change of medium. The conversion was carried out almost to completion in hepatocyte growth medium (Promocell GmbH) over a time period of 5-6 days (FIG. 2).

HPLC analysis of the substrates and their metabolites was carried out on an LC-MS system (Waters alliance HPLC-System with ZMD SingleQuad-MS (ESI+; cone voltage: 30 eV) using an RP HPLC column (Phenomenex Luna C18(2) 2×150 mm, 100 Å, precolumn: RP18; 4×3 mm). Required quantifications were used by means of calibration lines at compound-typical absorption maxima (diclofenac: $\lambda$max=270 nm; propranolol: $\lambda$max=220 nm). Using the eluant A (water+0.1% formic acid) and eluant B (acetonitrile) the linear HPLC gradient has the following composition: 5 min. (5% eluant B/95% eluant A), from 5 to 20 min. the mixture ratio of the mobile phase composition changes linearly to 100% eluant B. The flow rate was 0.5 mL/min (Hansen et al. (2013)).

Example 3

Production of the phase II metabolite 2-hydroxydesipramine β-D-glucuronide from desipramine through a two-step process. Combination of liver cells that have phase I biotransformation activity (primary liver cells or genetically modified liver cells) and recombinant phase II enzyme (UDP-glucuronosyltransferase)

In this sample embodiment the starting material desipramine was catalytically converted by genetically modified human liver cells to the phase I metabolite 2-hydroxydesipramine in a first reaction. In a following reaction, this intermediate was biotransformed into the phase II metabolite (glucuronide) in a cell bioreactor. This second reaction was carried out with the recombinant functionally active phase II enzyme (see FIG. 4a).

First, a reaction batch of 0.5 mL with the substrate desipramine was used (200 μM desipramine in Krebs-Henseleit buffer [25 mM NaHCO$_3$, 2 mM CaCl$_2$, 25 mM HEPES, pH 7.4, incubation 24 h, 0.5×10$^6$ liver cells]). The resulting product (2-hydroxydesipramine) was determined by LC-MS (λ=254 nm; M=282). This example involves a hydroxylation of desipramine at position 2 to form 2-hydroxydesipramine. In a second reaction, 2-hydroxydesipramine undergoes biotransformation by membrane-bound recombinant UDP-glucuronosyltransferase (produced through E. coli expression systems) to the phase II metabolite 2-hydroxydesipramine β-D-glucuronide. The reaction batch is consists of the following components: phosphate buffer 50 mM (pH 7); 0.5 mg/mL UDP-glucuronosyltransferase;

5 mM UDPGA; 1 mM MgCl. The phase II metabolite (2-hydroxydesipramine β-D-glucuronide, M=458) is detected by LC/MS (see FIG. 4b and FIG. 4c).

Example 4

Combination of peroxygenase system (purified phase I enzyme) and genetically modified liver cells to produce the phase II metabolite In this sample embodiment, the starting material desipramine was catalytically converted by fungal peroxygenases to the phase I metabolite 2-hydroxydesipramine, in a first reaction. In a following reaction, this intermediate was biotransformed into the phase II metabolite (glucuronide) using genetically modified liver cells in a cell bioreactor. This example illustrates the combined synthesis for human first-pass drug metabolites (phase I/II) from an enzyme- and cell-mediated biotransformation.

Reaction I was carried out using a reaction batch of 100 mL (5 mM substrate desipramine; peroxygenase of the fungus Agrocybe aegerita with an activity of 300 units; phosphate buffer 50 mM (pH 7); 4 mM ascorbic acid). After addition of the cosubstrate H$_2$O$_2$ (reaction activator; 5 mM) and a reaction time of 60 min. the resulting product (hydroxylated desipramine) was determined by LC-MS (λmax=254 nm). Thus, this example involves a hydroxylation of desipramine to the phase I metabolite 2-hydroxydesipramine. In the second reaction, cells (genetically modified liver cells) are used for biotransformation of 2-hydroxydesipramine to the phase II metabolite 2-hydroxydesipramine-β-D-glucuronide. The liver cells were preincubated in a hollow fiber bioreactor (CellFiber-System; area: 75 cm$^2$; cell count: 1×10$^8$ cells) for 7 days. Then, the substrate (100 μM) was applied through a change of medium. The conversion was carried out almost to completion in hepatocyte growth medium (Promocell GmbH) over a time period of 5 days. The phase II metabolite (2-hydroxydesipramine β-D-glucuronide, M=458) is detected by LC/MS (see FIG. 5).

The following generally applies for all detections:

The HPLC analysis of the substrates and their metabolites was carried out on an LC-MS system (Waters Alliance HPLC-System with ZMD SingleQuad-MS (ESI+; cone voltage: 30 eV) using an RP-HPLC column (Phenomenex Kinetex C18(2) 150 mm×4.6 mm, 100 Å, precolumn: RP18; 4×3 mm). Required quantifications were [carried out] by means of calibration lines at compound-typical absorption maxima using (diclofenac: λmax=270 nm; propranolol: λmax=220 nm, desipramine 254 nM). Using the eluant A (water+0.1% trifluoroacetic acid) and eluant B (acetonitrile+0.75% trifluoroacetic acid) the linear HPLC gradient has the following composition: 5 min. (5% eluant B/95% eluant A), from 5 to 20 min. the mixture ratio of the mobile phase composition changes linearly to 100% eluant B. The flow rate was 1.0 mL/min.

Detection:

i.) LC-MS system (Waters Alliance HPLC system with ZMD SingleQuad-MS (ESI+; cone voltage: 30 eV; column: Phenomenex Kinetex C18(2) 250×4, 6 mm, 5μ particle size, 100 Å; security guard: C18(2), 4×3 mm))

ii.) Desipramine (M=266), 2-hydroxydesipramine (M=282), 2-hydroxydesipramine β-D-glucuronide (M=458)

Example 5

Production of the phase II metabolite 5-hydroxypropranolol β-D-glucuronide from propranolol through a two-step process.

In this sample embodiment, the starting material propranolol was catalytically converted by fungal peroxygenases to the phase I metabolite 5-hydroxy propranolol, in a first reaction.

In a following reaction, this intermediate was biotransformed into the phase II metabolite (glucuronide) using genetically modified liver cells in a cell bioreactor. This example illustrates the combined synthesis for human first-pass drug active ingredient metabolites (phase I/II) from an enzyme- and cell-mediated biotransformation.

Reaction I was carried out using a reaction batch of 100 mL (5 mM substrate propranolol; peroxygenase of the fungus Agrocybe aegerita with an activity of 300 units; phosphate buffer 50 mM (pH 7); 4 mM ascorbic acid). After addition of the cosubstrate H$_2$O$_2$ (reaction activator; 5 mM) and a reaction time of 60 min. the resulting product (hydroxylated propranolol) was determined by LC-MS (λmax=280 nm). Thus, this example involves a ring hydroxylation of propranolol (M=259) to the phase I metabolite 5-hydroxy propranolol (M=275) (see FIG. 6a).

In the second reaction, genetically modified liver cells are used for biotransformation of 5-hydroxy propranolol to the phase II metabolite 5-hydroxy propranolol β-D-glucuronide. The hepatocytes were preincubated in a hollow fiber bioreactor (CellFiber-System; area: 75 cm$^2$; cell count: 1×10$^8$ cells) for 7 days. Then, the substrate (phase I metabolite, 100 μM) was applied through a change of medium. The conversion was carried out almost to completion in hepatocyte growth medium (Promocell GmbH) over a time period of 5-6 days. The phase II metabolite (5-hydroxy propranolol β-D-glucuronide, M=452) is detected by LC/MS (see FIG. 6b).

FIG. 1: A two-step process is shown to convert the substrate 7-ethoxycoumarin, through a phase I intermediate (7-hydroxycoumarin), to a phase II metabolite (7-hydroxycoumarin glucuronide). Reaction I (fungal peroxygenase module): the reaction is based on extracellular enzymes of fungal origin (peroxygenase; Agrocybe aegerita [1, 2]; reaction II (hepatocyte module): In a following reaction, the phase II metabolite (7-hydroxycoumarin glucuronide) is generated with a preparative 3D cell culture process (hollow fiber module system, Fibercell Inc.) with modified human liver cells (hepatocytes).

FIG. 2: HPLC chromatograms ($\lambda_{max}$=323 nm): Conversion of 7-ethoxycoumarin (ret. time=17.2 min.) to 7-hydroxycoumarin (ret. time=12.9 min.) with fungal peroxygenase ((A) reaction time: 0 h; (B) reaction time: 0.5 h) in the first reaction. The second following reaction shows the biotransformation of 7-hydroxycoumarin (ret. time=13.0 min.) to the phase II metabolite 7-hydroxycoumarin glucuronide (ret. time=11.6 min.) with human hepatocytes ((C) reaction time: 0 h; (D) reaction time: 24 h).

Figure 3:
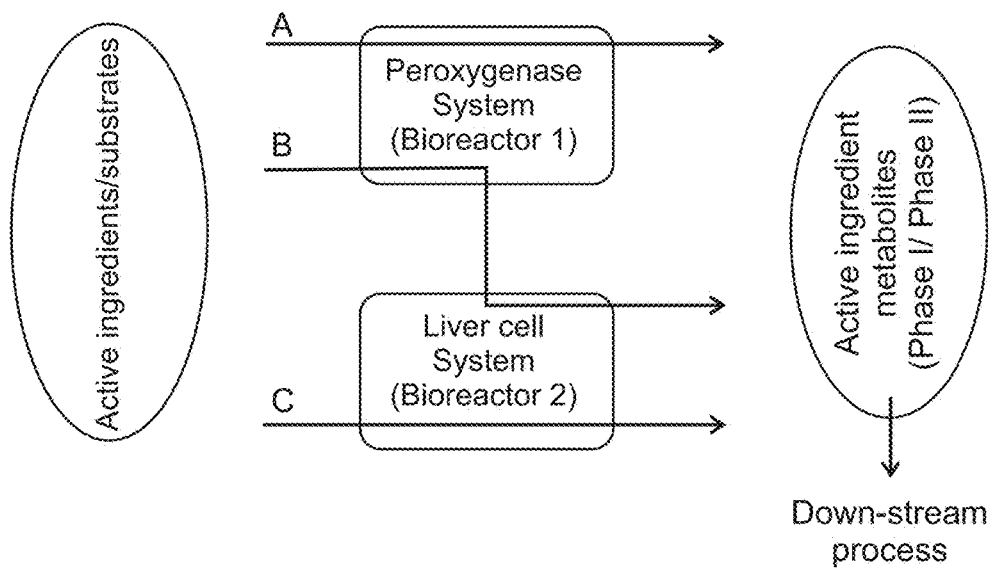

FIG. 3: Representation of the inventive principle.

Figure 4A:
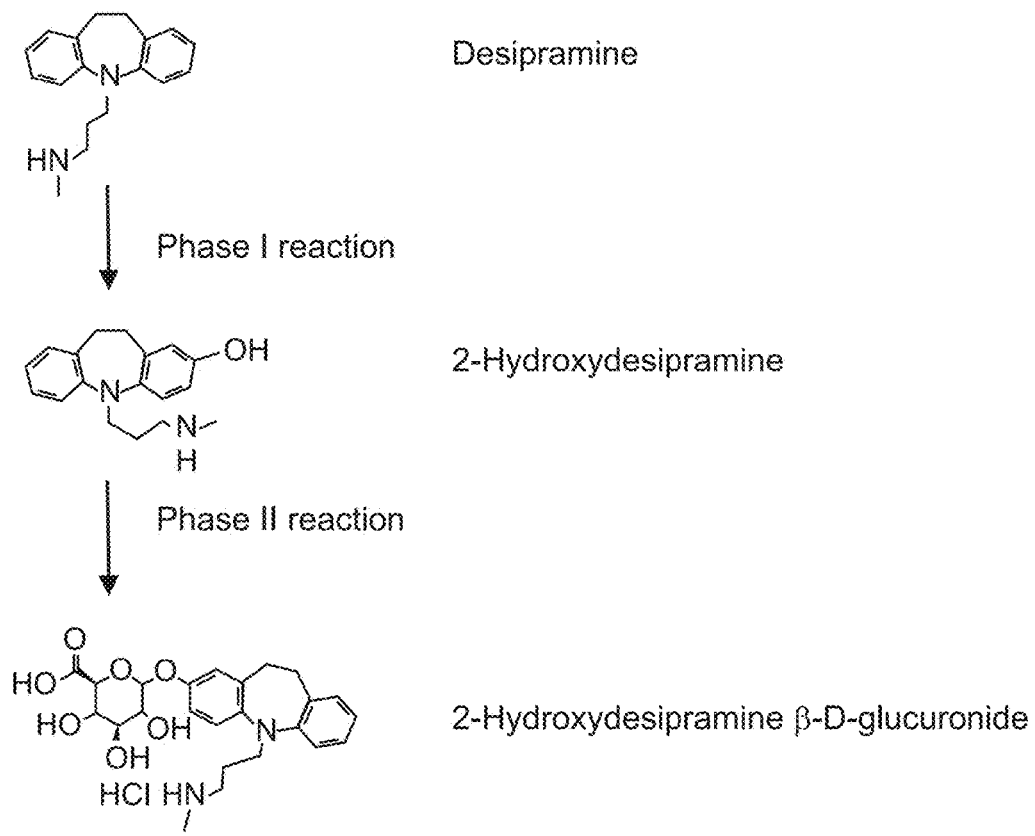

FIG. 4a: Reaction sequence of the selective conversion of desipramine.

Figure 4B:
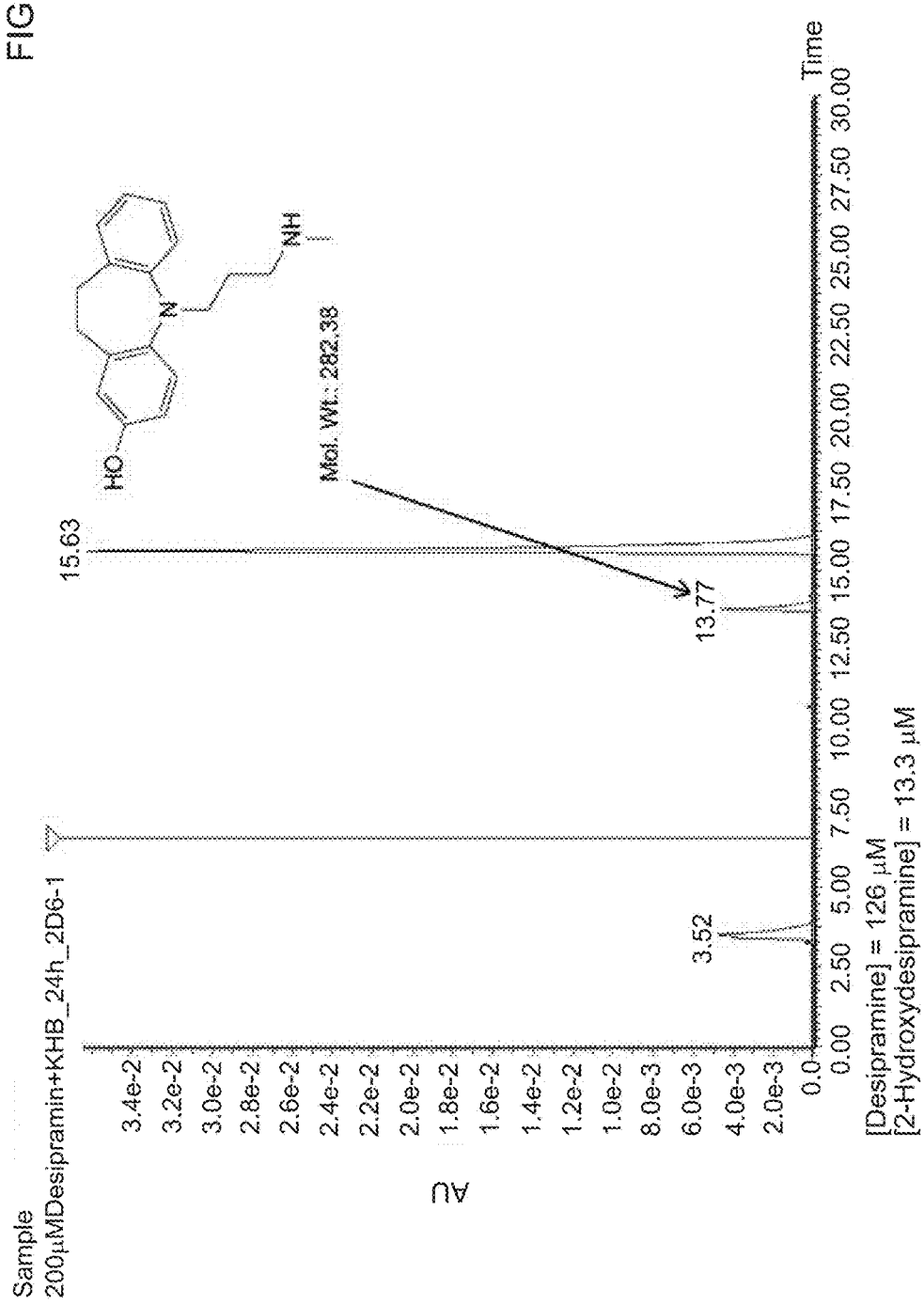

FIG. 4b: HPLC chromatogram of the conversion with desipramine to the phase I metabolite using genetically modified liver cells.

FIG. 4c: Mass spectrum demonstrating the conversion of desipramine using genetically modified liver cells.

Figure 5:
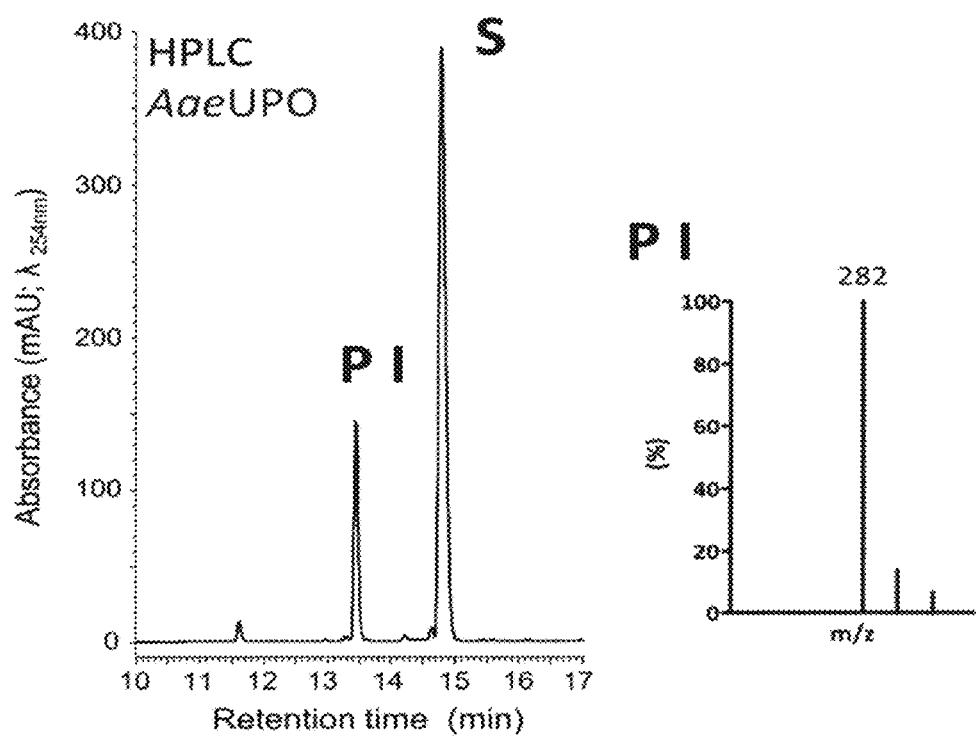

FIG. 5: Left, HPLC chromatogram for the conversion of desipramine using the peroxygenase system (AaeUPO=*Agrocybe aegerita* peroxygenase, S=substrate, desipramine, P1=product, hydroxylated desipramine, M=282), right LC-MS mass spectrum of the product.

Figure 6A:
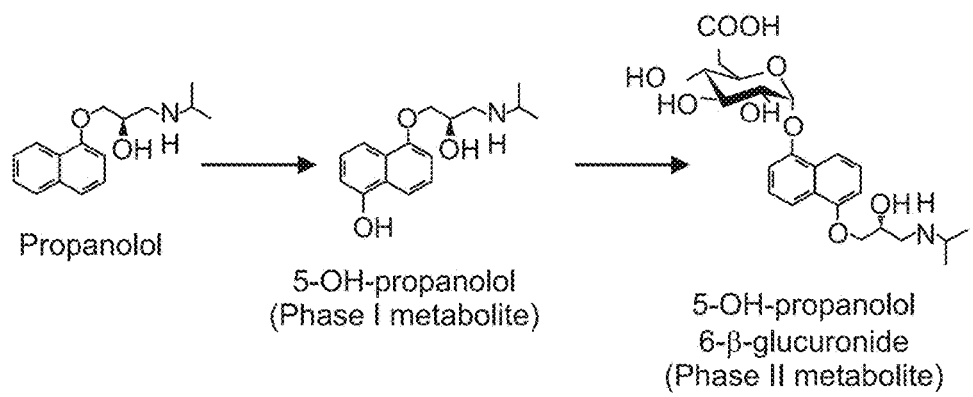

FIG. 6a: Reaction sequence of the selective conversion of propranolol.

Figure 6B:
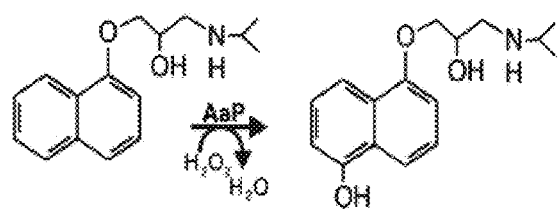
Figure 6B:
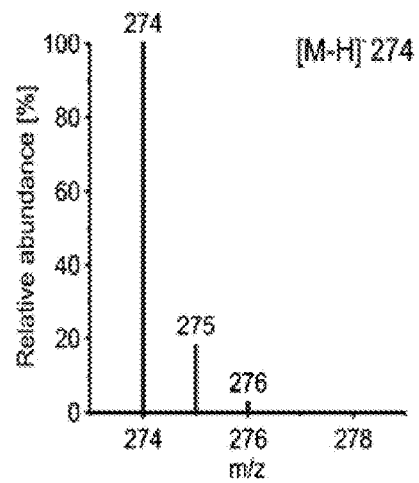

FIG. 6b: Mass spectrum on the conversion of propranolol to the phase I metabolite using peroxygenase enzyme system (Kinne et al. 2009).

LITERATURE CITED

1. Elaut G, Henkens T, Papeleu P, Snykers S, Vinken M, Vanhaecke T, Rogiers V (2006): Molecular mechanisms underlying the dedifferentiation process of isolated hepatocytes and their cultures. Current drug metabolism 7 (6): 629-60.
2. Arimoto R (2006): Computational models for predicting interactions with cytochrome p450 enzyme. Current topics in medicinal chemistry 6 (15): 1609-18.
3. Shimada T, Yamazaki H, Mimura M, Inui Y, Guengerich F P (1994): Interindividual variations in human liver cytochrome P-450 enzymes involved in the oxidation of drugs, carcinogens and toxic chemicals: studies with liver microsomes of 30 Japanese and 30 Caucasians. The Journal of pharmacology and experimental therapeutics 270 (1): 414-23.
4. Lamb D C, Waterman M R, Kelly S L, Guengerich F P (2007): Cytochromes P450 and drug discovery. Current opinion in biotechnology 18 (6): 504-12.
5. Chang C Y, Schiano T D (2007): Review article: drug hepatotoxicity. Alimentary pharmacology & therapeutics 25 (10): 1135-51.
6. Walker K, Ginsberg G, Hattis D, Johns D O, Guyton K Z, Sonawane B (2009): GENETIC POLYMORPHISM IN N-ACETYLTRANSFERASE (NAT): POPULATION DISTRIBUTION OF NAT1 AND NAT2 ACTIVITY. Journal of Toxicology and Environmental Health-Part B-Critical Reviews 12 (5-6): 440-472
7. Ullrich R, Kinne M, Hofrichter M, Scheibner K (2007): Verfahren zur O-Dealkylierung von Alkyarylethern. DE 10 2007 058 741.6.
8. Kinne M, Poraj-Kobielska M, Aranda E, Ullrich R, Hammel K E, Scheibner K, Hofrichter M (2009): Regioselective preparation of 5-hydroxypropranolol and 4'-hydroxydiclofenac with a fungal peroxygenase. Bioorganic & medicinal chemistry letters 19 (11): 3085-7.
9. Poraj-Kobielska M, Kinne M, Ullrich R, Scheibner K, Kayser G, Hammel K E, Hofrichter M (2011): Preparation of human drug metabolites using fungal peroxygenases. Biochemical pharmacology 82 (7): 789-96.
10. Hansen M, Herzog N, Miethbauer S, Schmidtke K U, Lupp A, Sperling S, Seehofer D, Damm G, Scheibner K, Küpper J-H (2013): Primary-like human hepatocytes genetically engineered to obtain proliferation competence display hepatic differentiation characteristics in monolayer and organotypical spheroid cultures. Drug metabolism and disposition: the biological fate of chemicals (submitted).
11. Burkard A, Dahn C, Heinz S, Zutavern A, Sonntag-Buck V, Maltman D, Przyborski S, Hewitt N J, Braspenning J (2012): Generation of proliferating human hepatocytes using Upcyte(R) technology: characterisation and applications in induction and cytotoxicity assays. Xenobiotica; the fate of foreign compounds in biological systems 42 (10): 939-56.

The invention claimed is:

1. A process to produce at least one biogenic substance in vitro, comprising:
   a) providing at least one starting material;
   b) adding at least one enzyme to the at least one starting material, thereby yielding a product;
   c) adding at least one liver cell to the product of b), or
   b') adding at least one liver cell to the at least one starting material, thereby yielding a product;
   c') adding at least one enzyme to the product of b'); and
   d) isolating at least one biogenic substance,
   wherein the at least one starting material comprises at least once chemical substance,
   and wherein the at least one enzyme is selected from the group consisting of oxidoreductases and biotransformation enzymes.

2. The process of claim 1, wherein the enzyme from b) and c') comes from a different organism than the liver cell doss.

3. The process of claim 1, wherein at least one bioreactor is used to carry out process steps b) and c), or process steps b') and c'), and at least one of steps b) and c), or at least one of steps b') and c'), can also be repeated or downstream.

4. The process of claim 3, wherein two or more bioreactors are used.

5. The process of claim 1, wherein the liver cell is selected from the group consisting of a cell containing at least one biotransformation enzymes, a human liver cell, a mammalian liver cell, genetically modified hepatocytes, proliferating liver cells, and liver cell lines.

6. The process of claim 5, wherein phase I enzymes comprise the cytochrome P450 system, alcohol dehydrogenases, aldehyde dehydrogenases, peroxidases, glutathione peroxidase, esterases, and hydrolases and/or phase II enzymes comprise glucuronyltransferases, sulfotransferases, glutathione S-transferase, methyltransferase, aminotransferases/transaminases, and acetyltransferases.

7. The process of claim 5, wherein the at least one biotransformation enzyme is phase I enzyme and/or phase II enzyme.

8. The process of claim 5, wherein phase I enzymes comprise the cytochrome P450 system, alcohol dehydrogenases, aldehyde dehydrogenases, peroxidases, glutathione peroxidase, esterases, and hydrolases and/or phase II enzymes comprise glucuronyltransferases, sulfotransferases, glutathione S-transferase, methyltransferase, aminotransferases/transaminases, and acetyltransferases.

9. The process of claim 1, wherein the at least one chemical substance is a pharmaceutical or active ingredient.

10. The process of claim 1, wherein the at least one chemical substance is an organic molecule.

11. The process of claim 1, wherein the oxidoreductases are monooxygenases, dioxygenases, oxidases, dehydrogenases, reductases, or peroxygenases.

12. The process of claim 1, wherein the biotransformation enzymes are phase I enzymes, phase II enzymes, esterases, hydrolases, or transferases.

\* \* \* \* \*